United States Patent [19]

Iwanski

[11] Patent Number: 4,692,335

[45] Date of Patent: Sep. 8, 1987

[54] CALCIUM HYPOCHLORITE TABLET

[75] Inventor: Donald P. Iwanski, Allison Park, Pa.

[73] Assignee: PPG Industries, Inc., Pittsburgh, Pa.

[21] Appl. No.: 771,868

[22] Filed: Sep. 3, 1985

[51] Int. Cl.$^4$ ............................................. A01N 25/00
[52] U.S. Cl. ..................................... 424/149; 424/464
[58] Field of Search .................. 424/149, 78; 514/464

[56] References Cited

U.S. PATENT DOCUMENTS

| | | | |
|---|---|---|---|
| 2,071,094 | 2/1937 | Vincent | 424/149 |
| 3,276,949 | 10/1966 | Robson et al. | 424/149 |
| 3,342,674 | 9/1967 | Kowalski | 424/149 |
| 3,495,948 | 2/1970 | Long et al. | 23/272.7 |
| 3,647,523 | 3/1972 | Horvath | 117/100 B |
| 3,793,216 | 2/1974 | Dychdala et al. | 424/149 |
| 3,856,932 | 12/1974 | May | 424/149 |
| 3,873,685 | 3/1975 | Kibbel et al. | 424/149 |
| 4,035,484 | 7/1977 | Faust et al. | 424/149 |
| 4,087,360 | 5/1978 | Faust et al. | 210/58 |
| 4,192,763 | 3/1980 | Buchan | 424/149 |
| 4,201,756 | 5/1980 | Saeman et al. | 424/149 |
| 4,281,421 | 8/1981 | Nyquist et al. | 424/149 |
| 4,469,848 | 9/1984 | Hooper et al. | 424/78 |

FOREIGN PATENT DOCUMENTS 1395010 5/1975 United Kingdom .

Primary Examiner—Shep K. Rose
Attorney, Agent, or Firm—Irwin M. Stein

[57] ABSTRACT

Novel solid articles comprising a compressed mixture of granular calcium hypochlorite and from about 0.5 to about 5.0 weight percent, basis the calcium hypochlorite, of solid wax binder selected from the group consisting of microcrystalline hydrocarbon wax and alkali metal salts of oxidized microcrystaline hydrocarbon wax are described. The novel solid articles are provided in the shape of, for example, tablets, which are prepared by dry blending the granular calcium hypochlorite and wax binder and feeding the mixture to a tableting press. The articles dissolve at a controlled rate, depending on the amount of binder used, in water, thereby providing a source of available chlorine over an extended period of time.

12 Claims, No Drawings

CALCIUM HYPOCHLORITE TABLET

DESCRIPTION OF THE INVENTION

The present invention relates to calcium hypochlorite compositions and, more particularly, relates to a solid calcium hypochlorite article, such as a tablet, which provides a continuous source of available chlorine for disinfecting and sanitizing water supplies over an extended period of time.

Calcium hypochlorite enjoys a major portion of the market for available chlorine compounds, aside from chlorine itself, because it is the cheapest and most stable solid composition known which delivers all of its available chlorine immediately on contact with oxidizable materials. Calcium hypochlorite compositions containing at least 65 weight percent of calcium hypochlorite have been on the market for many years and are used primarily as a commercial bleaching and sanitizing agent, particularly in the disinfection and sanitizing of water supplies such as swimming pool water. As a source of available chlorine, calcium hypochlorite is a highly soluble material which dissolves rapidly in water.

For the treatment of residential swimming pool water, it is conventional to broadcast granular calcium hypochlorite periodically directly on the water in the pool in quantities sufficient to maintain the available chlorine at or above the desired levels, e.g., from less than 1 part per million to a few parts per million of chlorine. In an alternative method, tablets of calcium hypochlorite are placed in the skimmer or in dissolving baskets around the swimming pool to provide continuous contact between the pool water and the solid calcium hypochlorite. A further method used to treat swimming pool water is to add granular or tabletted calcium hypochlorite to a dispensing device in which the calcium hypochlorite is contacted with the water to be treated so that dissolution of the calcium hypochlorite is controlled to form a solution of the desired available chlorine concentration. This concentrated solution is then added to the total body of pool water to provide the desired available chlorine concentration.

When added to water at room temperatures, calcium hypochlorite dissolves rapidly. Consequently, treatment of water, e.g., swimming pool water, is required almost daily to maintain a disinfecting or sanitizing quantity of available chlorine in the swimming pool. A source of calcium hypochlorite which provides a relatively constant source of available chlorine over a prolonged period, e.g., 4–6 or 7 days, is a highly desirable feature for the consumer and ultimate user of calcium hypochlorite.

It has now been discovered that a compressed mixture of granular calcium hypochlorite and from about 0.5 to about 5 weight percent, basis the calcium hypochlorite, of a solid wax binder selected from the group consisting of microcrystalline hydrocarbon wax and alkali metal salts of oxidized microcrystalline hydrocarbon wax provides an article which, when placed in contact with water, dissolves more slowly than an article composed of binder-free compressed granular calcium hypochlorite. When such articles are placed in the skimmer or in a dissolving basket used at a swimming pool installation, dissolution of the calcium hypochlorite in the article is prolonged for from 4 to 6 days during which time the article provides a source of available chlorine in amounts sufficiet for disinfecting and sanitizing, i.e., a disinfecting amount.

DETAILED DESCRIPTION OF THE INVENTION

Granular calcium hypochlorite is commercially available and generally contains from at least about 60 to about 70 percent by weight of calcium hypochlorite. The remainder of the calcium hypochlorite article of commerce is typically composed of varying amounts of sodium chloride, calcium chloride, calcium hydroxide, calcium chlorate and water. The aforementioned salts (other than calcium hypochlorite) are incorporated into the commercial calcium hypochlorite product during its synthesis and manufacture. Water may comprise between about 2 and about 15 percent, e.g., between about 4 and 10 percent of the calcium hypochlorite product.

In forming the article of the present invention, granular calcium hypochlorite is blended with the binder material and compacted with pressure into the shape desired, e.g., a tablet. The granular calcium hypochlorite should be free-flowing to allow it to be introduced into the compaction device, and such material may exhibit a relatively broad particle size distribution. The latter physical property permits the smaller particles to fill in the spaces between the larger particles during compaction. It is preferred that the particles comprising the granular calcium hypochlorite be particulate rather than powdery in size since the size of the particles compacted is believed to influence the rate of dissolution of the compacted article.

As a general guideline, the particles may have a principal size distribution between about minus 6 and plus 100 U.S. Sieve Series, i.e., the particles vary in size principally between about 0.13 inches (3.3 millimeters) and about 0.006 inches (0.15 millimeters). More commonly, the particles will have a principal size distribution between about minus 6 and plus 60 U.S. Sieve.

Particularly suitable for use in producing articles of the present invention is granular calcium hypochlorite having a size distribution of minus 10, and plus 45 U.S. Sieve Series, i.e., the granules are principally between about 0.08 and 0.014 inches (1.98 and 0.35 millimeters). Particles smaller than 60 U.S. Sieve present in the granular calcium hypochlorite represent a minor percentage, usually less than 2 percent, of the material charged to the compaction device.

The binders used to agglomerate the granular calcium hypochlorite in accordance with the present invention are microcrystalline hydrocarbon waxes and alkali metal, e.g., sodium and potassium, salts of oxidized microcrystalline hydrocarbon waxes. Microcrystalline wax consists of high molecular weight saturated aliphatic hydrocarbons, e.g., hydrocarbons containing about 48 carbon atoms. These waxes are available commercially and are produced by deoiling and cutting petrolatums or pipe still bottoms. The oxidized microcrystalline waxes are prepared by oxidizing the microcrystalline wax with air in the presence of a catalyst such as manganese or cobalt.

The wax binder is used in amounts of between about 0.5 and about 5.0 weight percent, basis the calcium hypochlorite. Typically, the higher the amount of binder used within that range the longer is the dissolution time for the calcium hypochlorite compositions of the present invention. Hence, varying the amount of binder in said compositions controls their rate of dissolution in water, such rate being adjustable with the amount of binder used. For residential swimming pools, binder levels of between about 0.5 and 2 weight percent are useful. Such binder levels will provide dissolution times of between about 4 and 6 or 7 days. Preferably between about 0.75 and about 1.75, e.g., 1.5, weight percent of the aforesaid wax binder is used. The microcrystalline waxes used herein as binders are available as finely-divided powders and are available commercially as the Petrolite ® series of microcrystalline hydrocarbon and modified hydrocarbon waxes. These microcrystalline waxes have a melting point of between about 95° C. and 105° C.

The articles of the present invention are prepared by dry blending granular calcium hypochlorite and the solid wax binder in a suitable blender and feeding the resulting mixture to conventional size-enlargement equipment such as a molding press, tableting press, roll-type press, pellet mill and screw extruder.

To assist in releasing the compressed calcium hypochlorite article from the forming equipment, it may be convenient to incorporate a small amount of lubricant (mold release agent) with the granular calcium hypochlorite-microcrystalline hydrocarbon wax blend or to dust the molds of the forming equipment with such agents. Typical lubricants that may be used include metal salts of fatty acids, e.g., fatty acids having at least 10 carbon atoms such as metal salts of stearic acid. The cation of the metal salt should be compatible with calcium hypochlorite, e.g., sodium, magnesium, zinc, and calcium. The proportion of lubricant utilized may be between about 0.1 and about 1.0 percent by weight.

The compressed article of the present invention may be prepared in any convenient desired shape, e.g., a brick, briquette, triangle, pellet, tablet, etc., depending upon the intended use of the article. Preferably, the shape is that of a tablet. The compressed article of the present invention may typically have a mass of between about 250 and about 350, e.g., about 300, grams of which at least about 94 percent, more typically at least 96.5 percent, is the granular calcium hypochlorite. The compressed article may be of a size which may be inserted readily into a skimmer or dissolving basket used with swimming pools or dissolvers used to form concentrated solutions of calcium hypochlorite. In the case of a tablet, it is preferred that the diameter of such tablet be between about 3 inches (7.6 centimeters) and about 3.5 inches (8.9 centimeters), e.g., between about 3.125–3.25 inches (7.9–8.3 centimeters), and be about 1 to 2 inches (2.5–5.1 centimeters), e.g., 1.25 inches (3.2 centimeters) thick. The compacted article preferably has a density of from about 1.6–2.3 grams per cubic centimeter (g/cc), e.g., 1.8–2.2 g/cc, more preferably about 2 g/cc. Generally, the denser the compacted article, the slower the dissolution of the article.

Solid articles of compressed granular calcium hypochlorite prepared in accordance with the present invention will dissolve slowly over a period of between about 4 and 6 or 7 days, depending on the ultimate mass of the article and the amount of binder used, when placed in a conventional skimmer used in association with swimming pools and contacted with circulating pool water. The slow dissolution of the aforesaid article thereby provides a source of available chlorine for disinfecting and sanitizing the pool water over the period of time required to dissolve substantially all of the calcium hypochlorite in the article, e.g., a tablet. In a preferred embodiment, the solid article is prepared in a manner such that at least 10 weight percent of the original compressed calcium hypochlorite will remain after about 6 days of such use. More preferably, the calcium hypochlorite article provides a relatively constant source of chlorine to the pool water so as to maintain from about 1 to 2 parts per million of chlorine therein.

The present invention is more particularly described in the following examples which are intended as illustrative only since numerous modifications and variations therein will be apparent to those skilled in the art.

EXAMPLE 1

An eight quart V-blender was charged with 6.5 pounds of granular calcium hypochlorite having a size distribution of minus 6 and plus 100 U.S. Sieve Screen size and about 65% available chlorine. The desired level of additive was added to the calcium hypochlorite in the blender and covered with a second 6.5 of the same granular calcium hypochlorite. The blender was closed and ran for 45 minutes to blend the ingredients. The blend was charged to a Stokes R-tablet press having a die 2.5 inches (6.35 centimeters) in diameter and 1 inch (2.54 centimeters) in depth and tablets produced from the blend using a tableting pressure of 20 tons (18.1 metric tons). The additives and their amounts are listed in Table I.

TABLE I

| Additive | Amount, Wt. % | Tablet Wt., Grams[e] |
| --- | --- | --- |
| 1. None | 0 | 170 |
| 2. Calcium Stearate | 1 | — |
| 3. Calcium Stearate | 2 | — |
| 4. Microcrystalline Wax[a] | 1.5 | 184 |
| 5. Modified Microcrystalline Wax[b] | 1.5 | 177 |
| 6. Synthetic Clay[c] | 2 | — |
| 7. Calcium Carbonate | 2 | — |
| 8. Chlorinated Paraffin[d] | 2 | — |

[a]Petrolite ® X-2010
[b]Petrolite ® X-5082
[c]Laponite ® hectorite
[d]Chlorowax ® 70
[e]Average of 10 Tablets Dissolution rate of the tablets (except 2 and 3) was measured by placing one tablet in a skimmer basket mounted in a plastic pail through which water at room temperature (about 24° C.) was circulated from a 55 gallon (0.21 cubic meters) drum and monitoring the available chlorine level in the circulating water.

The control tablet was exhausted in one day as were the calcium carbonate, Chlorowax ® 70, and Laponite ® clay modified tablets. The calcium stearate modified tablets were brittle and of such poor quality with respect to physical integrity that their dissolution rates were not measured. The microcrystalline wax modified tablets had significantly slower dissolution rates—about 90 percent of the tablet being exhausted in about six days.

EXAMPLE 2

Calcium hypochlorite tablets modified with 1.5 weight percent Petrolite ® X-2010 microcrystalline wax and having a tablet weight of about 292 grams were prepared from granular calcium hypochlorite having a size distribution of minus 10 and plus 100 U.S. Sieve and about 65% available chlorine in accordance with the procedure used in Example 1 except that a tableting pressure of 45 tons (40.7 metric tons) and a die having a diameter of 3.125 inches (7.94 centimeters) and depth of 2 inches (5.1 centimeters) was used. About 98 percent of the granular product was in the range of minus 10 and plus 45 U.S. Sieve. The dissolution rate of such tablets were tested by the technique described in Example 1. The pH and temperature of the circulating solution for test A were maintained at about 7.5 and 24° C. respectively. For test B, the pH and temperature were about 7.7 and 23°-24° C. Results for two of such dissolution rate tests are tabulated in Table II.

TABLE 2

| Test A | | Test B | |
| --- | --- | --- | --- |
| Elapsed time, Hours | Ave. Avail. Chlorine, ppm. | Elapsed time, Hours | Ave. Avail. Chlorine, ppm. |
| 0 | 33.3 | 0 | 19.8 |
| 24.65 | 383.0 | 24.65 | 358.1 |
| 49.01 | 485.8 | 49.0 | 446.8 |
| 89.54 | 581.5 | 89.5 | 595.7 |
| 115.0 | 691.5 | 115.0 | 691.5 |
| 137.5 | 762.4 | 137.4 | 744.7 |
| 162.3 | 783.7 | 162.2 | 751.8 |

The data of Tables I and II show that microcrystalline wax-modified calcium hypochlorite tablets had significantly slower dissolution rates than unmodified tablets and provided chlorine to the circulating aqueous medium for from about 6 to 7 days, depending on the total weight of the tablet.

Although the present process has been described with reference to specific details of certain embodiments thereof, it is not intended that such detail should be regarded as limitations upon the scope of the invention except as and to the extent that they are inclined in the acompanying claims.

What is claimed is:

1. A solid article comprising a compressed mixture of granular calcium hypochlorite and from about 0.5 to about 5.0 weight percent of a solid wax binder selected from the group consisting of microcrystalline hydrocarbon wax and alkali metal salts of oxidized microcrystalline hydrocarbon wax.

2. The article of claim 1 wherein the principal size distribution of the granular calcium hypochlorite is between minus 6 and plus 100 U.S. Sieve.

3. The article of claim 2 wherein the binder is present in amounts of from about 0.75 to 1.75 weight percent.

4. The article of claim 3 wherein the binder is the potassium salt of oxidized microcrystalline hydrocarbon wax.

5. The article of claim 3 wherein the mass of the article is from 250 to 350 grams.

6. The article of claim 5 wherein the shape of the article is in the form of a tablet having a diameter of from about 3 to about 3.5 inches.

7. The article of claim 1 wherein at least 10 weight percent of the original mass of compressed calcium hypochlorite remains after 6 days of contact with water.

8. The article of claim 1 wherein the granular calcium hypochlorite is at least 65 weight percent calcium hypochlorite.

9. The article of claim 2 wherein the principal size distribution of the granular calcium hypochlorite is between minus 10 and plus 45 U.S. Sieve.

10. The article of claim 9 wherein the binder is present in amounts of from 0.75 to 1.75 weight percent.

11. The article of claim 10 wherein the density of the article is between about 1.6 and 2.3 grams per cubic centimeter.

12. The article of claim 10 wherein the principal size distribution of the granular calcium hypochlorite is between minus 6 and plus 60 U.S. Sieve.

* * * * *